United States Patent [19]
Boyd et al.

[11] Patent Number: 5,797,917
[45] Date of Patent: Aug. 25, 1998

[54] ANTERIOR SPINAL INSTRUMENTATION AND METHOD FOR IMPLANTATION AND REVISION

[75] Inventors: Lawrence M. Boyd; Thomas McGahan, both of Memphis, Tenn.

[73] Assignee: SDGI Holdings, Inc., Wilmington, Del.

[21] Appl. No.: 799,792

[22] Filed: Feb. 12, 1997

Related U.S. Application Data

[63] Continuation-in-part of Ser. No. 482,447, Jun. 7, 1995.

[51] Int. Cl.⁶ ................................................. A61B 17/88
[52] U.S. Cl. ............................. 606/99; 606/79; 606/179
[58] Field of Search ........................... 606/61, 79, 80, 606/82, 99, 176, 179, 180; 623/17

[56] References Cited

U.S. PATENT DOCUMENTS

| | | | |
|---|---|---|---|
| 493,730 | 3/1893 | MacKenzie | 606/179 |
| 3,848,601 | 11/1974 | Ma et al. | 128/305 |
| 4,696,308 | 9/1987 | Meller et al. | 128/754 |
| 4,820,305 | 4/1989 | Harms et al. | 623/16 |
| 4,877,020 | 10/1989 | Vich | 128/92 |
| 5,015,247 | 5/1991 | Michelson | 128/92 |
| 5,196,014 | 3/1993 | Lin | 606/61 |
| 5,197,967 | 3/1993 | Wilson | 606/79 |
| 5,261,909 | 11/1993 | Sutterlin et al. | 606/61 |
| 5,397,364 | 3/1995 | Kozak et al. | 623/17 |
| 5,423,823 | 6/1995 | Schmeiding | 606/80 |
| 5,484,437 | 1/1996 | Michelson | 606/61 |
| 5,632,747 | 5/1997 | Scarborough et al. | 606/79 |

*Primary Examiner*—Michael Buiz
*Assistant Examiner*—David O. Reip
*Attorney, Agent, or Firm*—Woodard, Emhardt, Naughton Moriarty & McNett

[57] ABSTRACT

A system and method for anterior fixation of the spine utilizes a cylindrical implant engaged in the intradiscal space at the cephalad and caudal ends of the construct. The implants are cylindrical fusion devices (10) filled with bone material to promote bone ingrowth and fusion of the disc space. An attachment member (40) is connected to each of the fusion devices (10) and a spinal rod (50) is connected to each of the attachment members using an eyebolt assembly (53, 54, 55). In a further inventive method, a revision of the construct is achieved by removing the fusion devices. Each fusion device is engaged by an elongated guide member (62) over which a cylindrical trephine (70) is advanced. The trephine (70) is used to extract a core (84) of bone material around the fusion implant, while the guide member (62) is used to remove the bone core (84) containing the fusion implant (10). In another aspect of the invention, a removal insert (90, 90') is provided that engages an implanted fusion device (10). The removal insert (90, 90') can be used to guide the trephine (70) around the fusion device, and is connected to a removal tool (100) once the bone core is created. The removal tool (100) includes a shaft (101) attached to the removal insert (90, 90'), and a slap hammer (104) slidably mounted on the shaft.

15 Claims, 9 Drawing Sheets

1

ANTERIOR SPINAL INSTRUMENTATION AND METHOD FOR IMPLANTATION AND REVISION

REFERENCE TO RELATED APPLICATIONS

This application is a continuation-in-part of U.S. patent application Ser. No. 08/482,447 entitled ANTERIOR SPINAL INSTRUMENTATION AND METHOD FOR IMPLANTATION AND REVISION, filed Jun. 7, 1995, owned by the assignee of the present application.

BACKGROUND OF THE INVENTION

The present invention concerns a spinal instrumentation system utilizing elongated members extending along the length of the spine and attached to multiple vertebrae by fixation elements, such as bone screws. In particular, the invention concerns anterior instrumentation, together with a surgical technique for implanting the instrumentation. The invention also contemplates a surgical revision technique for this spinal instrumentation.

Historically, correction of spinal disorders and treatment of spinal injuries was approached posteriorly, or namely from the back of the patient. Initially, the anterior approach to spinal instrumentation, that is from the front and side of the patient, was not favored, due to the unfamiliarity of this approach to spinal surgeons and due to the fear of severe complications, such as neurovascular injury or compromise of the spinal cord. However, in the face of some reported difficulties in addressing correction of thoracolumbar and lumbar scoliotic curvatures from a posterior approach, surgeons sought anterior forms of correction and stabilization. One such technique was developed by Dwyer in Australia during the 1960's in which a staple-screw construct was applied to the convex side of the scoliotic curvature. The screws were connected by a cable and correction was obtained by applying compressive forces at each instrumented level. The anterior spinal compression produced tensile forces within the cable which in turn generated a corrective bending moment at each of the vertebral levels.

On the heels of Dwyer's success, other anterior instrumentation followed. Further, surgeons began to recognize that certain spinal treatments were best approached anteriorly, rather than posteriorly. Anterior approaches give direct access to the intervertebral disc space for anterior release and interbody fusion. Presently, common indications for anterior instrumentation include: lumbar scoliosis with deficient posterior elements; thoracolumbar curves with extreme lordosis; paralytic thoracolumbar scoliosis requiring both an anterior and a posterior fusion; thoracolumbar spine trauma, such as burst fractures; and degenerative conditions of the vertebral body. In the case of burst fractures, it is known that neurocompression occurs from the anterior direction. Further, anterior debridement of fracture fragments is frequently believed to be a more effective means to decompress the spinal canal, as opposed to known posterior techniques.

Since the initial Dwyer instrumentation, many anterior plate and rod systems have been developed, such as the systems of Dunn, Kostuik-Harrington, Zielke and Kaneda. Many of these systems permit dynamic distraction of the vertebrae followed by direct compression of implanted bone graft contained within the resected disc space and after decompression of the neural elements.

Many of these anterior systems can lead to complications. Some of the more prominent problems that have occurred involve failure of the fixation components, and an often high incidence of loss of reduction or correction. Many of the difficulties in this respect can be traced to the vertebrae instrumented at the end of the construct where the loads on the instrumentation are the greatest. In some cases, bicortical purchase of vertebral body screws has been found to assure a more solid fixation at the ends of the construct and to protect against dislodgement of the screws. There does, however, still remain a need for an anterior instrumentation that can provide adequate correction of spinal deformities and that can be easily implanted. In addition, the system must ensure a strong fixation that will not deteriorate over time resulting in a loss of correction.

In some cases, it has been found that revision surgery is necessary, even when following the best possible surgical implantation of the instrumentation. Frequent indications for revision of spinal instrumentation include extension of existing instrumentation, and replacement of failed implants. In the cases involving early spinal implants, revision required cutting away the spinal implants. As implant design became more sophisticated, capabilities were developed for revision surgery that was relatively safe to the patient and non-destructive to implants, particularly those implants that were intended to be retained.

In systems using bone screws, revision surgeries can significantly compromise the vertebral body. In addition, in certain anterior approaches where stronger fixation is essential, revision procedures to replace failed components may necessarily compromise the new construct.

In view of these difficulties, there is a need for a spinal fixation system that is readily suited for revision surgery. Specifically, the system must be suitable for the addition or removal of components by way of revision without sacrificing either an existing construct or eliminating the possibility of implanting a new, more stable construct. In addition, there is a need for revision techniques that permit complete removal of a construct once fusion has occurred, again without compromising the spine or the implants.

SUMMARY OF THE INVENTION

To address these needs, the present invention contemplates a method for anterior fixation of the spine commencing with a thoracoabdominal exposure of the spinal segments to be instrumented. In the preferred embodiment, fusion devices are implanted within the cephalad and caudal disc spaces after a total discectomy. The fusion devices are configured to contain bone growth material to promote bone ingrowth and consequently fusion of the instrumented disc spaces. These cephalad and caudal fusion devices serve as anchors to ensure a stable and solid anterior construct.

In accordance with the method, bone screws are engaged within the vertebral bodies of the intermediate vertebrae. Preferably, the bone screws are variable angle screws having a cancellous threaded portion that is long enough to engage both lateral cortices of the respective vertebrae. An attachment member is provided having a head portion configured substantially similar to the head portion of the variable angle screw. In the preferred embodiment, eyebolt assemblies are used to attach and fix the head portions of the variable angle screws and the attachment members to an elongated spinal rod. The rod is positioned posteriorly of the head portions and is offset from the longitudinal axis of the fusion implant. It has been found that this anterior system and surgical technique provides a more reliable and complete decompression of the spinal canal. The use of the fusion devices as anchors at the ends of the construct renders this anterior instrumentation a viable alternative to address spinal conditions previously reserved for treatment from a posterior approach.

The system in accordance with one embodiment utilizes a threaded cylindrical fusion implant that is placed between or threaded into the endplates of the adjacent vertebrae. The implant can be filled with morcellized autologous bone to promote fusion through the implant and between the vertebral endplates. One end of the fusion implant is laterally disposed and accessible for placement of an attachment member. In one embodiment, the exposed end has a threaded opening for receiving a threaded post of the attachment member. In accordance with one feature of the present invention, the attachment member also includes a head portion that is configured substantially similar to the head of the bone screw engaged in the intermediate vertebrae. The head portion defines a slot for receiving the body of an eyebolt assembly, and includes a pattern of radial serrations. The head portions of the fusion implant attachment members and the bone screws are engaged to the spinal rod by a variable angle connection member comprising an eyebolt, nut and splined washer. The attachment member provides a significant benefit in that it adapts a known fusion implant to appear and behave as a bone screw with enhanced rigidity and fixation.

In another aspect of the invention, a surgical technique for revision of the spinal instrumentation is contemplated. More specifically, the revision technique is applied to removal of a cylindrical fusion implant fused in an intradiscal space. The revision technique relies upon a guide member connected to the fusion implant in situ. A cylindrical trephine is concentrically disposed over the guide member for advancement to the implant site. The trephine has an inner diameter slightly larger than the outer diameter of the fusion implant.

With the fusion implant held by the guide member, and the member guiding advancement of the trephine, the trephine is rotated so that its cutting teeth progressively cut around the fusion implant and into the vertebral bone. Once the cutting teeth of the trephine is advanced past the end of the fusion implant, the trephine is withdrawn, leaving an excised core of bone surrounding the fusion implant. The guide member is used to finally extract the fusion device and its surrounding bone core. This defect can then be exactly filled with an appropriately sized bone plug or dowel. Preferably, the same trephine is used to obtain the bone plug from a solid bone mass, such as the iliac crest.

In a further aspect of the invention, the revision technique is augmented by the use of a removal insert. The removal insert engages the fusion implant in situ. The insert is configured to act as a guide for the trephine that is used to excise the core of bone surrounding the fusion implant. In accordance with this aspect of the invention, the insert is engaged to the implant and held in place while the trephine performs the bone excision. After the core of bone surrounding the fusion implant has been created, the trephine is removed and the removal insert is engaged to a shaft carrying a slap hammer slidable along the shaft. The slap hammer is used to repeatedly contact a handle at the opposite end of the shaft from the fusion device to facilitate removal of the fusion device and surrounding bone plug. This instrument and technique can be useful in instances where the bone plug created by the trephine is difficult to manually remove.

It is one object of the present invention to present a novel method for anterior instrumentation of the spine. A further object resides in features of the anterior technique and the implant system itself that provides a rigid and secure fixation of the spine, especially at the cephalad and caudal extremes of the system.

Another object is to provide a system that can capitalize on benefits of an intervertebral fusion device serving as an anchor to the system. Other objects and the significant benefits of the present invention will become apparent on consideration of the following written description and the accompanying figures.

DESCRIPTION OF THE PREFERRED EMBODIMENTS

Figure 1:
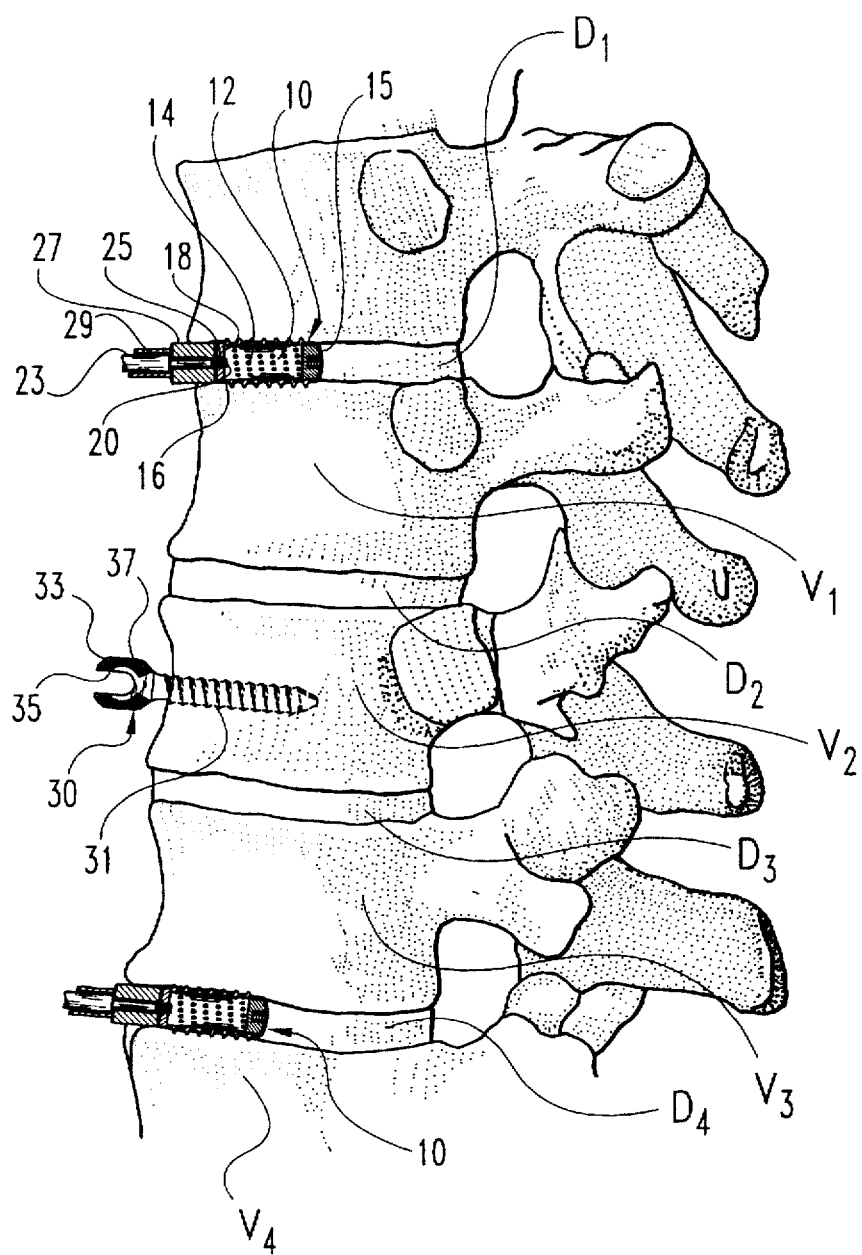
FIG. 1 is a view from the anterior aspect of a portion of the spine showing cylindrical fixation devices according to the present invention depicted in partial cross-section and implanted within a vertebral body and intradiscal spaces.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, initial steps of the surgical technique contemplated by the present invention are illustrated. In particular, the invention contemplates anterior fixation of several vertebral segments, identified as vertebra vertebrae $V_1-V_4$ and their adjacent discs $D_1-D_4$. This anterior instrumentation could be used, for instance, to correct a lumbar scoliosis condition followed by fusion of the affected vertebral levels. Initially, the lateral aspects of the vertebral bodies are revealed by way of a thoracoabdominal exposure. A discectomy can be performed on each of the disc spaces $D_1$–$D_4$, since these motion segments will be eliminated by the permanent stabilization implants.

Using calipers, the distance of the cortices of the intermediate vertebral bodies is determined to assess the length of the bone screw to be placed laterally into the vertebra. In this instance, the intermediate vertebra $V_2$ is instrumented with a variable angle screw 30. A preferred variable angle screw is described in detail in U.S. Pat. No. 5,261,909 to Dr. Chester Sutterlin, et al., which is owned by the assignee of the present invention. The disclosure of this '909 Patent is incorporated herein by reference as it pertains to the description of the variable angle screw 30 and its engagement to a spinal rod. For the purposes of the present disclosure, the variable angle screw 30 includes a bone engaging portion 31 or threaded shank which is sized to preferably span the distance between the cortices on the lateral sides of the vertebral body $V_2$. The screw 30 includes a head portion 33 which defines a slot 35 for receiving an eyebolt body therethrough. The head portion 33 also includes a plurality of radial splines 37 formed thereon for interdigitation with a corresponding washer to be discussed below.

In the illustrated embodiment, only four vertebral levels are instrumented. Consequently, the top and bottom most disc spaces $D_1$ and $D_4$ are instrumented with a hollow screw that is configured to enhance the degree of fixation to the adjacent vertebrae. In particular, the hollow screw includes a first portion in the manner of a cylindrical implant 10. Preferably this implant 10 is a fusion device that permits bone ingrowth for fusion and permanent fixation. In accordance with the preferred embodiment of the present invention, this cylindrical implant 10 is a threaded spinal implant as described in U.S. Pat. No. 5,015,247 of Dr. Gary Michelson. The disclosure of this implant in the '247 Patent is incorporated herein by reference. Other fusion devices are contemplated, such as the interbody fusion device of Dr. Kozak described in U.S. Pat. No. 5,397,364, which disclosure is incorporated herein by reference. This Kozak device, and other fusion devices, can be modified for lateral introduction into the intradiscal space for implementation in the present inventive surgical technique.

For purposes of the present invention, the cylindrical implant 10 defines a hollow interior chamber 12 which can be filled with bone graft material or bone chips. A plurality of apertures 14 are defined through the implant to communicate with the hollow interior to permit tissue ingrowth. A threaded end cap 15 encloses an open end of the implant to allow the implant to be filled and retain bone chips in the hollow interior chamber 12 prior to implantation. The exterior surface of the implant 10 includes bone engaging threads 16 formed thereon which are configured to be screw-threaded into the end plates of the adjacent vertebrae. The cylindrical implant 10 has a rear surface 18 which is exposed laterally when the implant 10 is threaded into the disc space $D_1$. This rear surface 18 defines a threaded opening 20 therethrough. Further details of the construction of this preferred cylindrical implant can be gathered from the '247 patent.

The cylindrical implant 10 can be implanted between the two pairs of adjacent vertebrae in the manner disclosed in the '247 Patent, which technique is described at cols. 9–10 and is incorporated by reference. Once the site has been prepared in the disc space, an insertion rod 23 having a threaded post 25 can be engaged to the threaded opening 20 in the rear surface 18 of the implant. A guide member 27 concentrically surrounds the insertion rod, with the rod specifically passing through bore 29 in the guide member. The insertion rod 23 and guide member 27 are used to drive each of the cylindrical implants 10 into their respective intradiscal spaces $D_1$ and $D_4$. Again, further details of the manner of implantation of the hollow implant 10 are disclosed more fully in the '247 Patent. It is understood that other similar intradiscal implants could be utilized, providing that the implant includes a threaded opening at its rear surface, such as the threaded opening 20 of rear surface 18, or some equivalent thereto. For example, the Kozak interbody fusion device of the '364 Patent incorporated above can be modified to include a similar threaded opening at a lateral face of the device.

Figure 2:
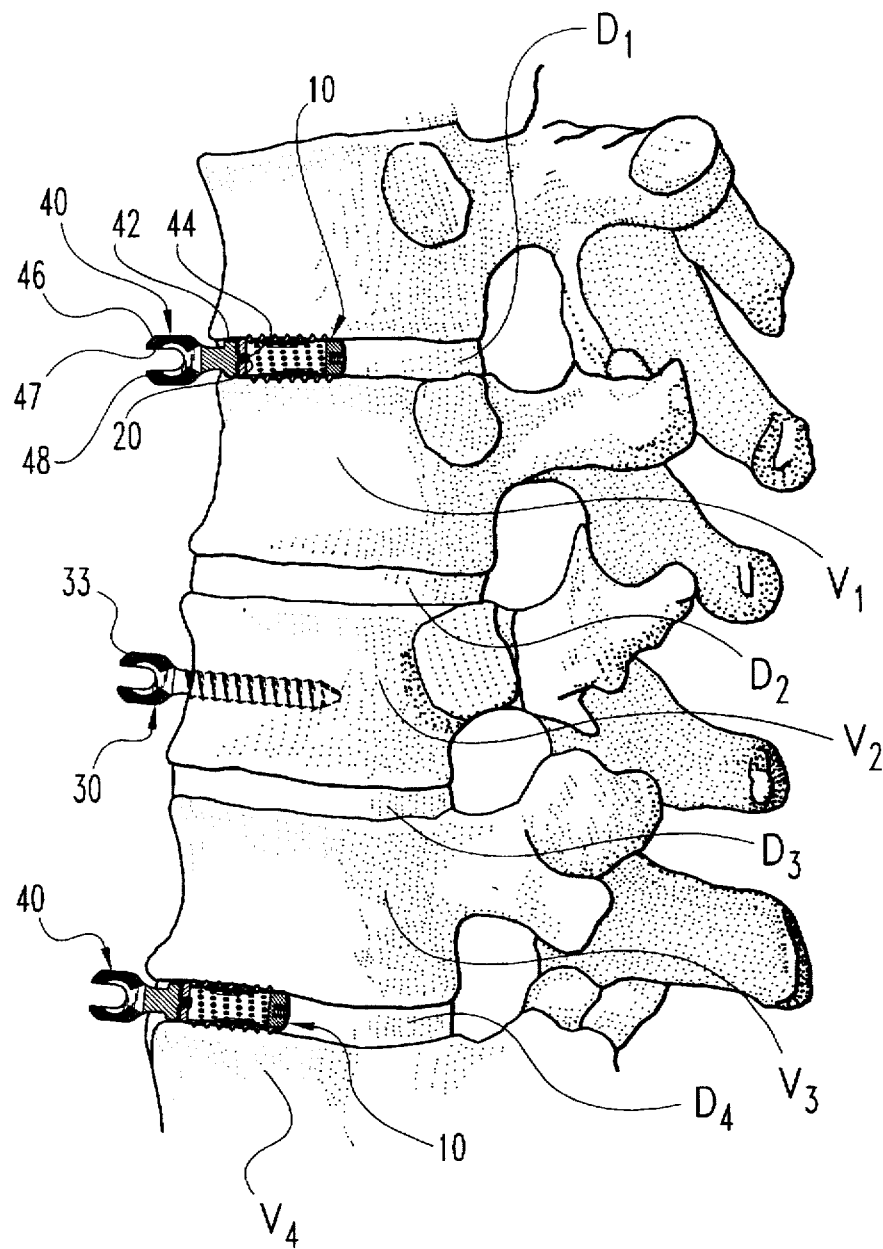
FIG. 2 is a view of the portion of the spine shown in FIG. 1 with additional components added to permit engagement of the fixation elements to an elongated rod.

Referring now to FIG. 2, the instrumented segments are seen with the hollow implants 10 fully disposed within the disc spaces $D_1$ and $D_4$. Likewise, the variable angle screw 30 is fully inserted into the vertebral body $V_2$. Preferably, the screw 30 sits with the screw head 33 flush against the lateral surface of the vertebra.

At the opposite anchoring ends of the construct, at disc spaces $D_1$ and $D_4$, an attachment head 40 is engaged to each cylindrical implant 10. Specifically, the attachment head 40 includes a base 42 from which projects a threaded stem 44. The threaded stem 44 is adapted to engage the threaded opening 20 in the rear surface 18 of the cylindrical implant 10. The attachment head 40 includes a head portion 46 which is substantially similar to the head portion 33 of the variable angle screw 30 described above. In particular, the head portion 46 includes an eyebolt slot 47 and is equipped with radial splines 48 on one surface of the head portion. Each of the cylindrical implants 10 receives a corresponding attachment head 40.

Figure 3:
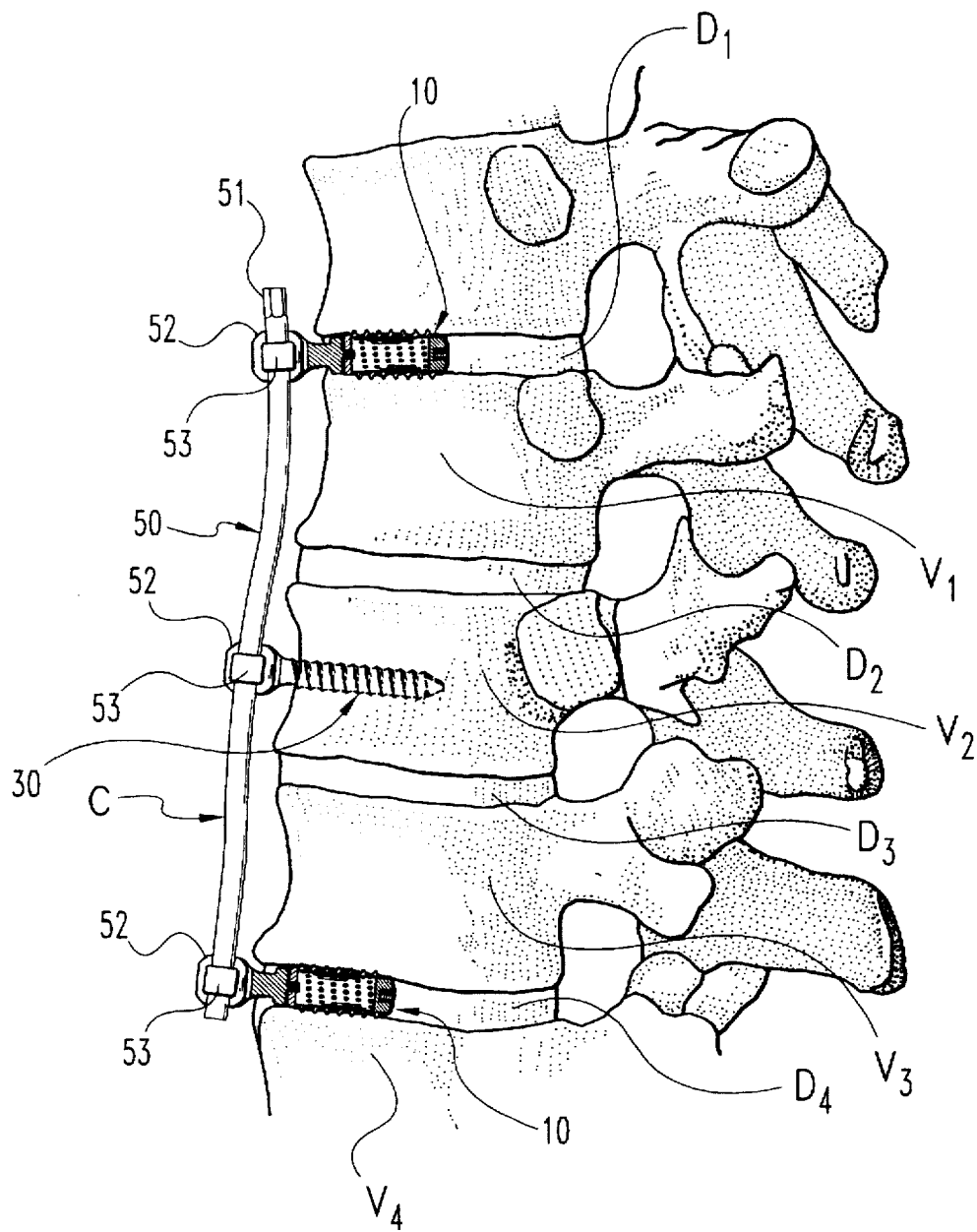
FIG. 3 is a view of the portion of the spine shown in FIG. 2 instrumented with a spinal rod extending between the three vertebral motion segments.

Preferably, the head portions 46 of the attachment heads 40 and the head portion 33 of the variable angle screw 30 are maintained in a straight line from the cephalad to the caudal ends of the instrumented segments. With the surgical approach of the present invention, it is not necessary to use specific derotation or screw placement techniques to produce a lordosis in the instrumented segments. Instead, as provided in the next steps of the procedure depicted in FIG. 3, a rod 50 is contoured at a curvature C to produce the lumbar lordosis or thoracic kyphosis in the sagittal plane. Generally, the rod 50 will be contoured to conform to the scoliotic curvature with the rod arranged on the concave side of the curvature. Once the rod has been contoured, it is attached to each of the head portions 33 and 46 by way of a splined washer 52 and connection member, preferably in the form of an eyebolt assembly. As shown in FIG. 3, the eyebolt assembly includes a body 43 which extends both through the splined washer 52 and through the slots 35 and 47 in the respective variable angle screw head portions 33 and attachment head portions 46. These details of the eyebolt construct are shown more clearly in FIG. 4. It is also recognized that this same eyebolt attachment assembly is described in the '909 Patent, which has been incorporated herein by reference.

Figure 4:
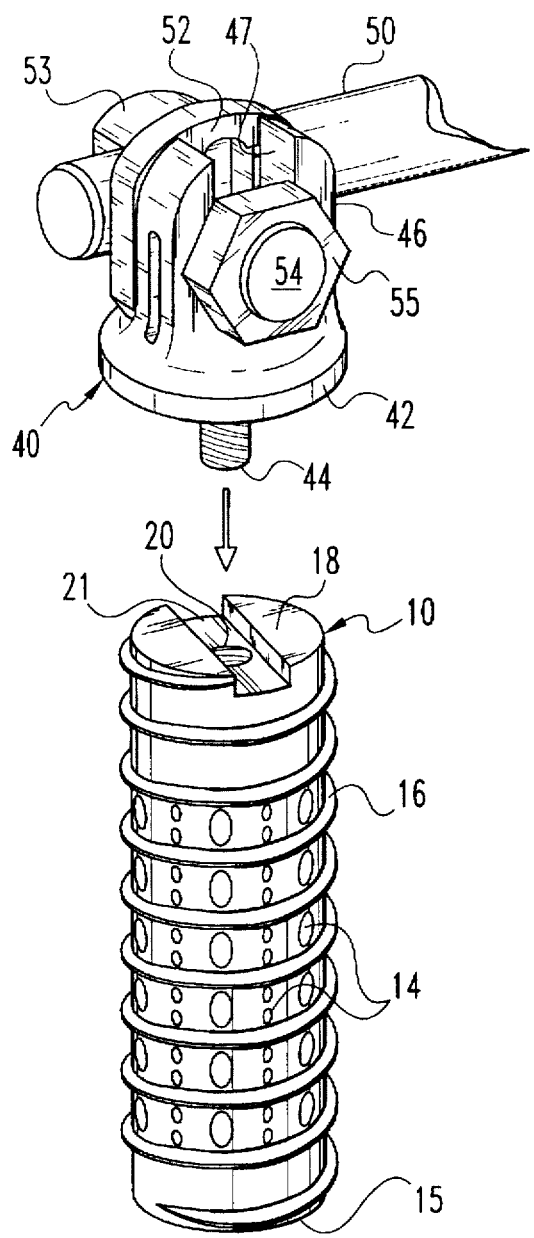
FIG. 4 is an exploded perspective view of a hollow screw and rod engaging elements as used in the construct depicted in FIG. 3.
Figure 5:
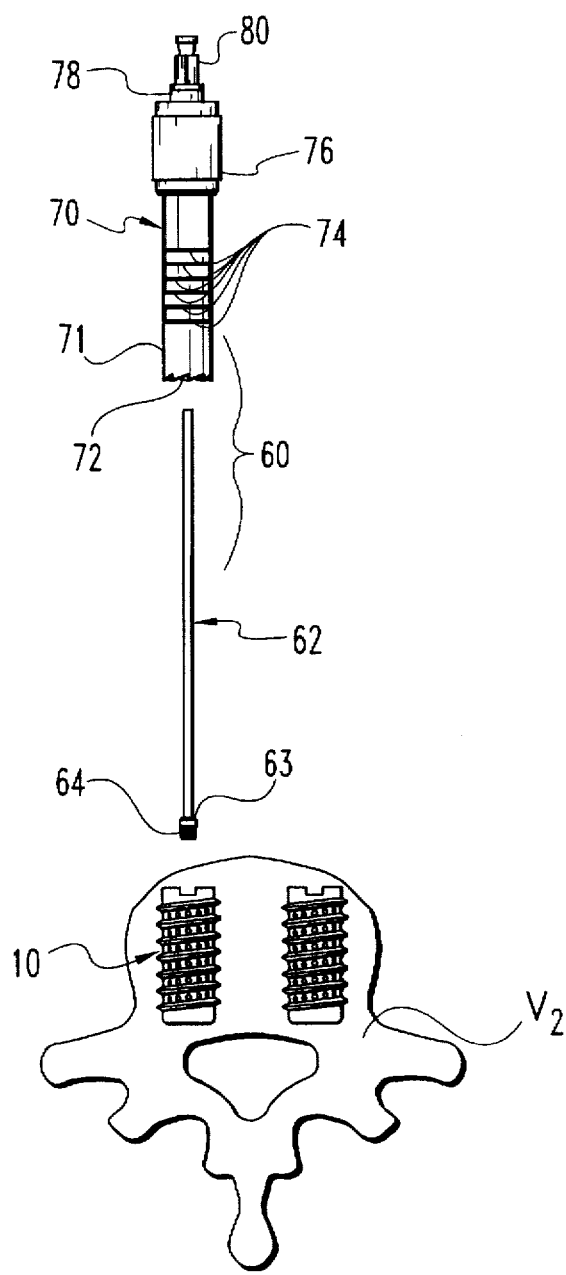
FIG. 5 is an exploded view of instrumentation configured for removal of a cylindrical fusion implant disposed between adjacent vertebrae as part of a revision technique in accordance with the present invention.

Referring to FIG. 4, it is seen that the attachment of the head portion 46 of the attachment head 40 is achieved with the splined face of the head portion facing toward the rod 50. The splined washer 52 is disposed between the rod and the splined face of the attachment head 40, more particularly with its corresponding splines interdigitating with the splines 48. As discussed more fully in the '909 Patent, the interdigitating splines allow the rod 50 to be oriented at a variety of angles in the sagittal plane relative to the attachment head 40. While FIGS. 1–3 depict the fixation screws as being generally parallel to each other for clarity, in reality the head portions 33 and 46 will be oriented at different angles in the frontal plane, depending upon the corrected spinal curvature.

The eyebolt assembly itself includes an eyebolt body 53 which includes an aperture for receiving the spinal rod 50. A portion of the eyebolt body 53 projects through the splined washer 52. Extending from the body is an threaded eyebolt stem 54 which receives a nut 55. Tightening the nut 55 on the stem 54 clamps the entire construct together, namely the rod 50, the splined washer 52 and the attachment head 40. A similar eyebolt arrangement is used to engage the variable angle screw 30, to the spinal rod 50.

At this step of the procedure, each of the eyebolts is tightened enough to seat the rod and the screw heads, while still allowing the rod to rotate within the apertures of the eyebolt assemblies. A hex end 51 is provided on the rod 50 so that the rod can be rotated while still attached to the variable angle screw 30 and the hollow screws 10. Rolling or rotating the rod in this manner translates the predefined scoliotic curvature into the sagittal plane to produce the requisite lordosis at the instrumented vertebral segments. Once the rod has been rolled to its proper position to produce the lordotic curvature, segmental decompression or compression can be applied to further correct any deformity in the frontal plane. It has been found that instrumenting the vertebral bodies from this anterior approach typically results in a more complete and reliable decompression of the spinal canal than with other approaches, such as a posterior instrumentation. Once the appropriate disc heights have been restored, along with the proper curvature in the frontal and sagittal planes has been achieved, the eyebolts are tightened to firmly clamp the rod 50 to each of the fixation elements attached to the spine.

In accordance with the preferred embodiment, the spinal rod is offset from the longitudinal axis of the cylindrical implant (i.e.—the axis extending through the threaded opening 20). Preferably, the spinal rod is positioned posteriorly to the head portions to which the rod is attached. This placement allows the eyebolt stem and nut to face anteriorly toward the abdominal cavity and away from more sensitive regions. (It should be noted that for clarity the head portions depicted in FIGS. 1–3 have been shown rotated 180° from this preferred orientation.)

Preferably, each of the hollow implants 10 is filled with morcellized bone graft material, such as autograft. Moreover, at the surgeon's option, the remaining disc space can also be filled with morcellized bone material. One object of using the hollow apertured cylindrical implant 10 and the bone graft material is to induce fusion across the intradiscal spaces. Once fusion occurs, the cylindrical implants 10 which provide the anchor at the opposite ends of the construct will be more rigidly secured to the spine than other known bone screw constructs. It is believed that the use of the fusion implant 10 at the intermediate vertebral segments is not essential, since the loads are not as harsh in the intermediate portions than at the ends of the instrumented vertebral segments.

In specific embodiments, the variable angle screw 30 can be 5.5, 6.5 or 7.5 mm cancellous screw. The cylindrical implants 10 can have an outer threaded diameter of between 10 mm–24 mm. Further, ¼ or 3–16 inch diameter rods can be used, together with appropriately sized eyebolt assemblies. It is of course understood that the length of the threaded cancellous portion of the variable angle screw, as well as the diameter of the cylindrical implants 10 is determined by the geometry of the particular instrumented vertebral segments. It is contemplated that the present inventive surgical technique can be used at all levels of the spine with appropriately sized implants.

It has been found that even with the best preoperative planning some revision of the fixation construct may be required. In addition, failure of the construct before fusion is complete may also necessitate a complete or partial revision of the implant. In some instances, the revision entails cutting away the spinal rod 50 and unthreading each of the bone screws engaged into the vertebrae. With the present inventive anterolateral approach and instrumentation, a more refined revision technique and instrumentation is available. Using the present construct, removal of the rod is made extremely simple and reduced simply to the step of loosening the eyebolts attached to each of the head portions at the various vertebral segments. The variable angle screw 30 is readily removed by unthreading the screw from the vertebral body $V_2$. At the cephalad and caudal ends of the construct, the attachment heads 40 are unscrewed from their respective cylindrical implants 10. To this point, the revision procedure is relatively simple. However, difficulties can arise in removing the cylindrical implants 10 from their respective intradiscal spaces $D_1$ and $D_4$. Removal of the implants is particularly more difficult if bone ingrowth has occurred between the vertebral end plates and the hollow anterior 12 of the implant.

Removal of these fusion implants 10 is one important feature of the novel revision technique of the present invention and the associated revision instruments 60. The instruments 60 include an alignment rod 62 which has a flared end 63 with a threaded post 64 projecting therefrom. The threaded post 64 is configured to engage the threaded opening 20 in the rear surface 18 of the cylindrical implant 10. In the revision procedure, the alignment rod 62 is engaged to the cylindrical implant 10 by way of the threaded post 64 and threaded opening 20.

With the alignment rod 62 so positioned, a trephine 70 is advanced over the rod. The trephine 70 includes a tubular cutting end 71 which defines a plurality of jagged cutting teeth 72. Preferably, the cutting teeth 72 are of known configurations for cutting through cortical bone as the cutting end 71 is rotated in the proper direction. The cutting end 71 further defines a plurality of depth markings or rings 74 which can be used to determine the depth of the trephine 70 in the intradiscal space. The trephine 70 includes a rotation collet 76 at the proximal end of the trephine which is concentrically disposed around the tubular body of the cutting end 71. The proximal end of the trephine also defines a driving boss 78 which is configured to receive a conventional driving tool or suitable wrench for rotating the cutting end. Finally, the nearmost end of the trephine 70 includes an alignment rod clamp 80 which is used to clamp the proximal end of the alignment rod 62 concentrically received within the trephine.

Figure 6:
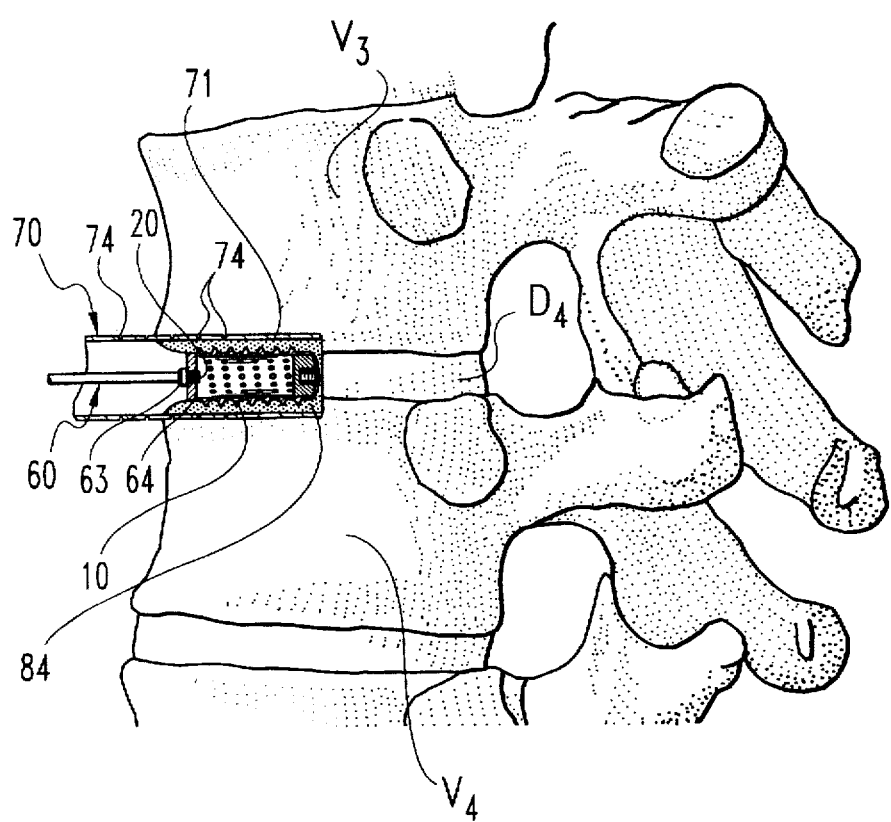
FIG. 6 is a view of a portion of the vertebral column depicted in FIG. 1 showing use of the instrumentation of FIG. 5 for removal of a hollow screw.
Figure 7:
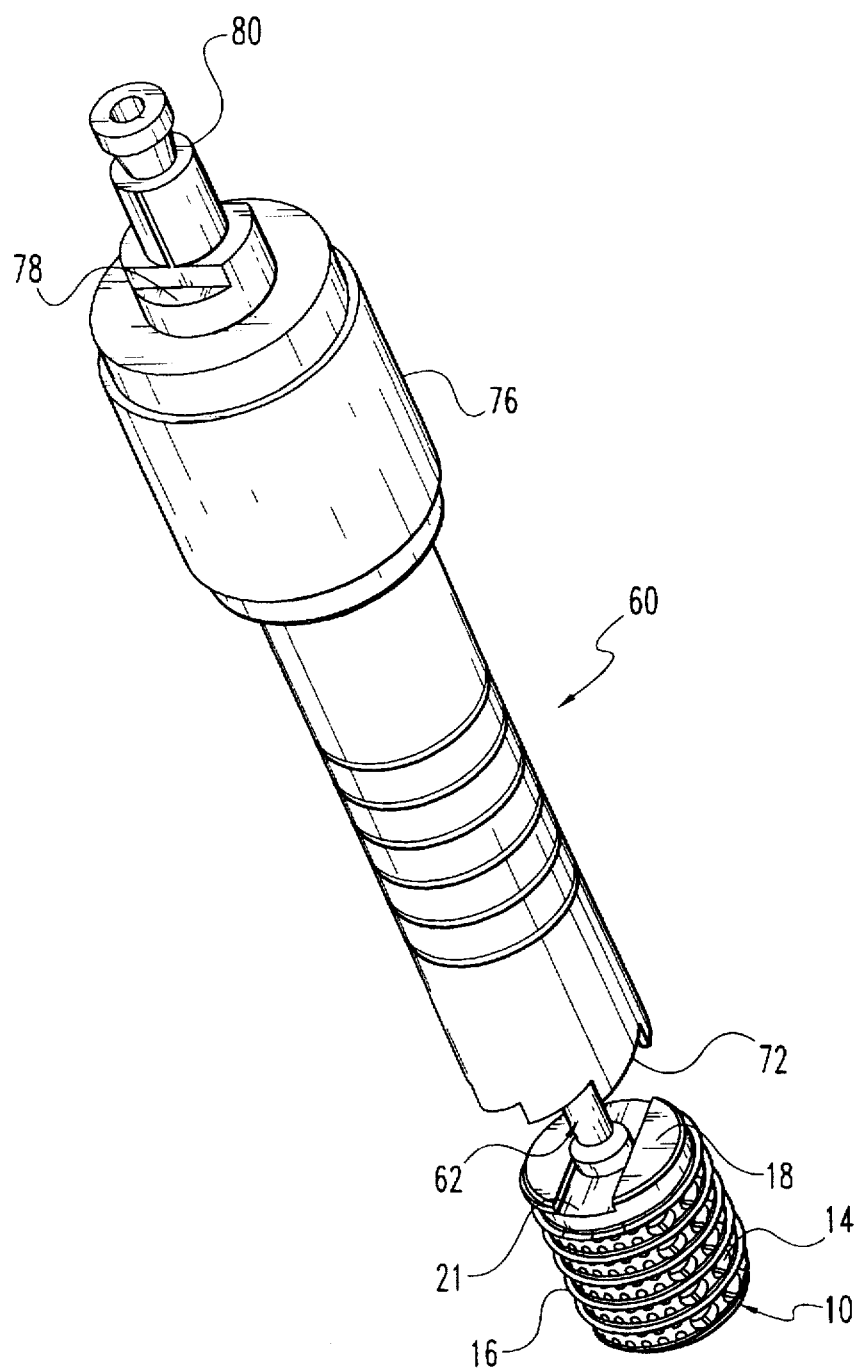
FIG. 7 is a perspective view of the removal instrument with the hollow screw engaged thereto.

Referring to FIG. 6, it can be seen that the alignment rod 62 is engaged with the cylindrical implant 10 disposed in the disc space $D_4$. The trephine 70 is advanced over the alignment rod 62 until the cutting edge 72 contacts the vertebral bodies $V_3$ and $V_4$. Rotation of the trephine causes the cutting teeth 72 to bore out a core 84 of bone material surrounding the cylindrical implant 10. The core 84 can then be removed together with the implant 10 by first withdrawing the trephine 70 and then pulling the alignment rod to remove the entire assembly. In FIG. 7, the cylindrical implant 10 is seen supported by the alignment rod 62 as the entire revision instrumentation 60 is withdrawn from the surgical site.

The depth markings 74 can be used to either limit or determine the depth of insertion of the trephine. In its depth limiting function, the depth of the distal end of the cylindrical implant is already known and is correlated to a particular one of the depth markings. The trephine is then advanced into the vertebrae until the appropriate depth marking is aligned with the vertebral body. The markings 74 can also be used interactively when the insertion of the trephine is monitored under indirect vision. Once it is seen that the cutting edge 72 of the trephine has passed the end of the cylindrical implant, the appropriate depth marking can be noted. Once the implant has been extracted, the noted depth marking is then used to determine the proper size of bone dowel to be extracted from another location to be inserted back into the intradiscal space.

Once the core 84 of bone and the cylindrical implant 10 has been excised from the disc space, an exactly fitted plug.or dowel can be reinserted into the remaining bore. The trephine 70 can be used to core out bone from the patient, such as at the iliac crest, which can then be reinserted using the same trephine. Once the trephine is removed, the adjacent vertebrae will collapse around the newly inserted bone plug. This bone dowel will retain the disc height and again permit fusion at the revision site. Moreover, once fusion occurs, the site of the bone plug may be strong enough to support new spinal implants.

The present revision technique carries a significant advantage in that it allows use of hollow cylindrical fusion implants at any position along the construct. It has been found that the use of fusion implants enhances the rigidity and strength of the fixation. This same increased rigidity and strength makes ordinary surgical revisions difficult or impossible to do without causing serious damage to what may be an otherwise healthy vertebral body. Use of the trephine 70 in accordance with the present technique eliminates this risk and permits easy and quick removal of the threaded cylindrical implant, even where fusion has occurred.

Figure 9:
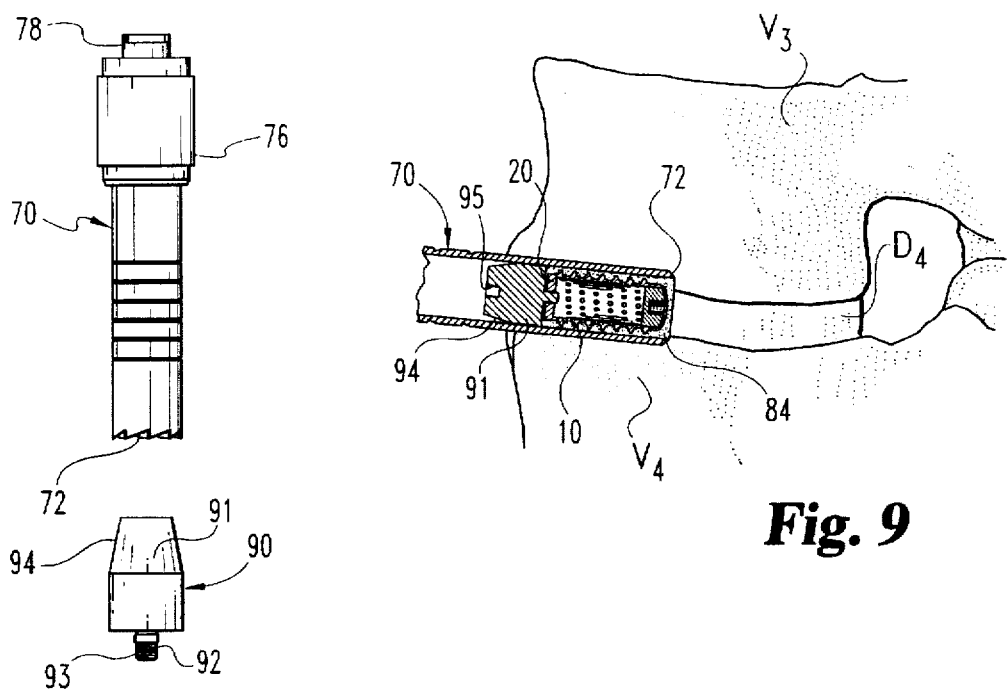
FIG. 9 is a cross-sectional view of a portion of the instrumentation shown in FIG. 8 showing the use of the instrumentation for removal of the implant.
Figure 8:
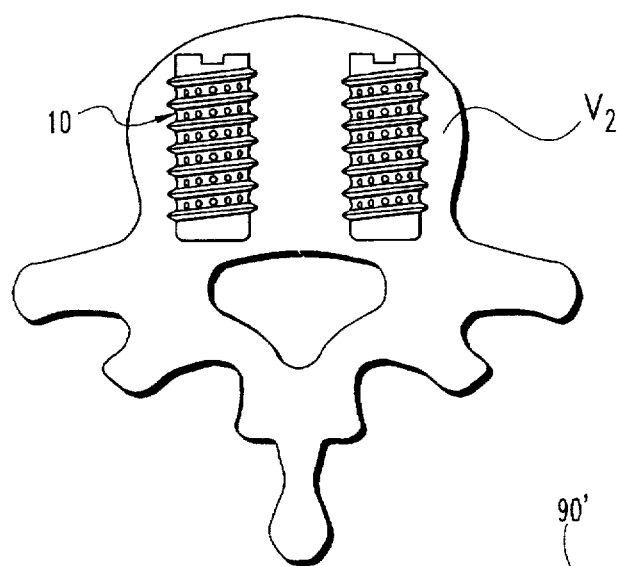
FIG. 8 is an exploded view of instrumentation according to a further embodiment of the invention configured for removal of a fusion implant disposed between adjacent vertebrae.

In a further embodiment of the invention, a removal insert 90 is provided as shown in FIGS. 8–9. The insert is engaged to the fusion implant 10 to facilitate removal of the implant and the bone plug generated by the trephine 70. In accordance with the preferred embodiment, the removal insert 90 includes a body 91 and an engagement portion 92 that is configured to engage the hollow screw or fusion implant 10. In one specific embodiment, the engagement portion 92 includes a threaded post 93 that is adapted to engage the threaded opening 20 of the implant 10. Again, in accordance with the preferred embodiment, the threaded post 93 is arranged so that the removal insert 90, and particularly the body 91, contacts the end face of the implant 10 to provide a firm connection between the two components.

The removal insert 90 is also provided with a frusto conical portion 94 integral with the body 91. This frusto conical portion 94 acts as a guide for the trephine 70 during the step of the revision technique in which a core of bone is excised surrounding the implant 10. In accordance with a preferred technique using the removal insert 90, the insert is engaged to a fusion implant, such as implant 10, by way of the threaded post 93. The trephine 70 can then be guided along the frusto conical portion 94 of the insert 90 until it contacts the vertebrae $V_3$ and $V_4$. The trephine 70 is operated in the manner described above, namely being rotationally driven into the bone to generate a core of bone 84 immediately surrounding the fusion implant 10.

Figure 11:
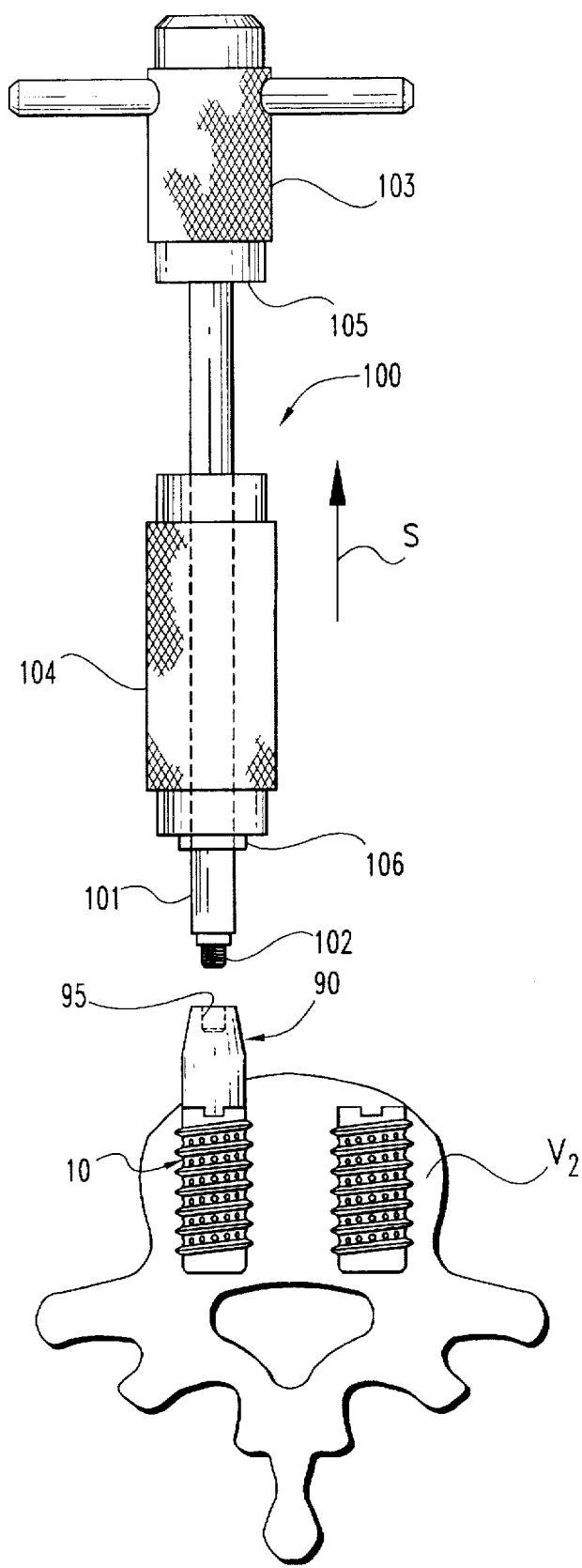
FIG. 11 is a side view of one embodiment of the invention showing a method and apparatus for removing an implant.

Once the core of bone 84 has been created, the trephine 70 can be removed and a removal tool 100 utilized as shown in FIG. 11. The removal tool 100 includes an elongated shaft 101 terminating in a threaded post 102 at one end and a handle 103 at an opposite end. The threaded post 102 is configured to engage a threaded bore 95 in the frusto conical portion 94 of the removal insert 90. The removal tool 100 further includes a slap hammer 104 that is slidably disposed along the elongated shaft 101. The slap hammer 104 is utilized by driving the hammer upward in the direction of the arrow S toward the handle 103. When the slap hammer 104 strikes the contact surface 105 of the handle 103, it imparts a removal force along the shaft 101, through the removal insert 90 and to the fusion device 10 and its surrounding bone core. In the revision surgery, a few taps from the slap hammer 104 will progressively dislodge or unseat the core of bone 84 and the fusion implant 10 from the disc space D4 and adjacent vertebrae. In one specific embodiment, the removal tool 100 is provided with a stop 106 that is engaged to the elongated shaft 101. The stop 106 restricts movement of the slap hammer 104 toward the removal tool 90, or more particularly the surgical site. The stop 106 can be integral with the shaft 101 or it can be a component that is added separately, such as in the form of an O-ring. That is, threaded onto the shaft 101 after the slap hammer 104 has been mounted on the removal tool 100.

Figure 10:
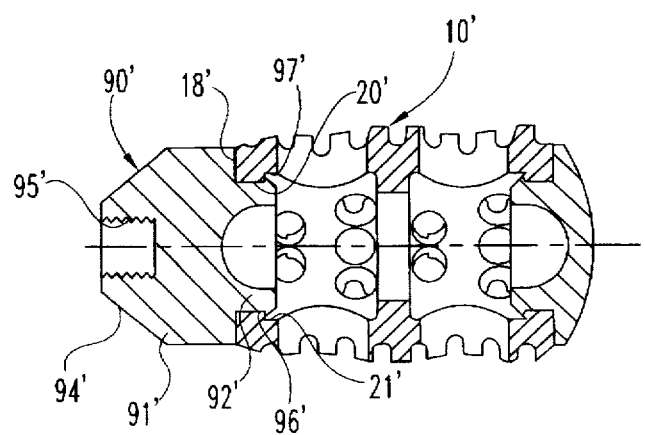
FIG. 10 is a side cross-sectional view of a removal insert in accordance with the embodiment shown in FIG. 8, modified to engage a different fusion implant or hollow screw.

The removal insert and associated technique can be applied to remove hollow screws or fusion devices of alternative design. One such alternative design is shown in FIG. 10 in which a removal insert 90' is engaged to a modified fusion implant 10'. The modified implant 10' includes a rear portion 18' defining an opening 20' therethrough. The implant 10' includes an interior recess 21' adjacent the opening 20'. To accommodate this modified implant, the removal insert 90' includes a body 91' and an engagement portion 92' that is configured to engage the opening 20' of the fusion implant 10'. The insert 90' also includes a frusto conical portion 94' and threaded bore 95' similar to the embodiment 90 in FIG. 8. In this respect, the alternative removal insert 90' is adapted to be engaged by the removal tool 100 shown in FIG. 11.

In this alternative embodiment, the removal insert 90', and particularly the engagement portion 92', defines a mating ring 96'. The mating ring 96' is sized to be received within the opening 20' of the fusion implant 10'. The mating ring 96' also preferably includes an engagement tab 97' that is configured to engage the interior recess 21' of the implant 10'. In this manner, the engagement portion 92' is solidly engaged to the implant 10'. The mating ring 96' and engagement tab 97' can be in the form of a continuous annular feature, or may also be in the form of a plurality of arms extending from the body 91'. In either case, the mating ring 96' must be sufficiently resilient to allow the engagement tabs 97' to be pushed through the opening 20' until they snap outward into the interior recess 21' of the fusion cage 10'. Once the removal insert 90' is engaged to the modified fusion cage 10', the remaining steps of the revision technique can be performed in the manner described above.

In the illustrated embodiments, the frusto-conical portions 94, 94' and the engagement portions 92, 92' are integral with the body 91. Alternatively, these portions can be separately attached to the body. For example, the threaded post 93 could itself be threaded into a bore at the bottom of the body, as could the mating ring 96', thereby providing a degree of interchangeability to the removal insert 90, 90'.

The present invention further contemplates other means for engaging the removal tool to the removal insert. In the illustrated embodiment, a threaded post 102 engages a threaded bore 95, 95' in the removal inserts 90, 90'. Other engagments can be utilized, such as resilient prongs or a press-fit, with appropriate mating features defined on the removal insert.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, in the preferred embodiment of the anterior instrumentation technique a hollow cylindrical fusion implant is used to support the attachment heads for engagement to a spinal rod. However, other intradiscal implants of various configurations may be used provided that the implants permit bone ingrowth. Further, while a spinal rod is disclosed, other longitudinal fixation elements, such as spinal plates, may be utilized in performing this inventive anterior technique.

With respect to the revision technique disclosed herein, the preferred embodiment of the procedure is performed in connection with the disclosed anterior instrumentation. However, the same revision procedure can be used to remove other fusion implants in other settings, with appropriate modification to the trephine to accommodate variations in implant configuration. This inventive technique has particular application, however, in removing fusion implants that engage the endplates or cortical bone of the vertebral body. It is understood that these same apparatus and techniques can have application for the removal and revision of other devices disposed within bone other than in the spine.

Further in accordance with the several aspects of the invention, and particularly of the revision technique and associated instrumentation, the removal insert can be configured to engage a variety of hollow screws or fusion devices. It is of course understood that only two specific embodiments of the fusion implant has been discussed above. The same inventive techniques can be adapted for removal and revision of non-cylindrical devices. It is also understood that the engagement portion of the removal inserts can be modified according to the engagement features of the fusion implant. It may be contemplated, for example, that only a friction fit is required between the engagement portion of the removal insert and the end of the fusion implant.

The removal insert, and particularly its body, can also assume various configurations depending upon the nature of the trephine to be used in the revision technique. Likewise, the engagement between the removal insert and the shaft of the removal tool can assume a variety of forms other than the mating threads of the specific depicted embodiment. It is of course understood that the engagement between the shaft and the removal insert must be sufficiently strong so that the use of the slap hammer does not cause the removal tool to disengage from the removal insert. Further, the slap hammer can assume a variety of configurations other than the elongated cylindrical form depicted in FIG. 11. For example, the slap hammer can simply be a disc having a circumferential size and shape that can be readily grasped and manually operated.

Furthermore, the removal tool 100 can be directly engaged to the device disposed within bone, such as device 10, after the core of bone has been cut by the trephine. In this instance, the removal of the core of bone and device embedded within the core proceeds in the manner described above. In particular, repeated striking of the slap hammer 104 against the contact surface 105 will extract the core of bone. However, the use of the removal insert 90, 90' stabilizes the device and the removal procedure.

In the preferred method, the trephine is first removed after the core of bone has been cut, and then the device and bone core are extracted. In an alternative embodiment, the trephine can be removed together with the removal tool, fusion device and surrounding bone core. This approach is particularly useful when the fusion device is removed using the alignment rod 62.

What is claimed is:

1. An apparatus for removal of a fusion implant in the disc space between adjacent vertebrae, comprising:

a guide member having an elongated shaft and an engagement end having means for engaging the fusion implant within the disc space to permit removal of the implant from the disc space by the guide member; and a cylindrical trephine concentrically disposed about said guide member, said trephine having a cutting end adjacent said engagement end of said guide member, said cutting end defining teeth for cutting a core of bone from the the adjacent vertebrae surrounding the fusion implant.

2. The apparatus for removal of a fusion implant of claim 1, wherein said cylindrical trephine includes depth markings defined on an outer surface of said trephine for gauging a depth of insertion of said cutting end into the adjacent vertebrae.

3. The apparatus for removal of a fusion implant of claim 1, wherein said trephine includes a clamp for engaging said shaft of said guide member.

4. The apparatus for removal of a fusion implant of claim 1 further comprising:

a contact surface associated with said guide member disposed apart from said engagement end; and a slap hammer slidably disposed on said shaft between said engagement end and said contact surface, said slap hammer operable to strike said contact surface when said guide member is engaged to said fusion implant to dislodge the device from the disc space.

5. The apparatus for removal of a fusion implant of claim 4 further comprising a stop attached to said shaft between said contact surface and said engagement end to restrict movement of said slap hammer along said shaft toward said engagement end.

6. An apparatus for removal of a device disposed within bone, comprising:

a guide member having a body with conical portion at one end and an engagement portion at an opposite end configured to engage the device disposed within bone to permit removal of the device from the bone by the guide member;

cylindrical trephine concentrically disposed about said guide member, said trephine having a cutting end adjacent said engagement end of said guide, member, said cutting end defining teeth for cutting a core of bone surrounding the device.

7. The apparatus for removal of a device disposed within bone of claim 6, wherein said cylindrical trephine includes depth markings defined on an outer surface of said trephine for gauging a depth of insertion of said cutting end into the bone.

8. The apparatus for removal of a device disposed within bone of claim 6, wherein said guide member has an outer diameter that is substantially equal to an outer diameter of the device disposed within bone.

9. The apparatus for removal of a device disposed within bone of claim 8, wherein said trephine has an inner diameter sized for a close running fit over said outer diameter of said guide member.

10. The apparatus for removal of a device disposed within bone of claim 6 further comprising:

an elongated shaft having an engagement end configured to engage said guide member and a contact surface disposed apart from said engagement end; and a slap hammer slidably disposed on said shaft between said engagement end and said contact surface, said slap hammer operable to strike said contact surface when said guide member is engaged to the device to dislodge the device from the disc space.

11. The apparatus for removal of a fusion implant of claim 10 further comprising a stop attached to said shaft between said contact surface and said engagement end to restrict movement of said slap hammer along said shaft toward said engagement end.

12. A removal insert for engagement between a device disposed within bone and a removal tool, said insert comprising:

a body having a substantially cylindrical portion with a first end and an opposite second end;

a conical portion attached to said body at said first end; and an engagement portion attached to said body at said second end, said engagement portion configured to engage the device disposed within bone.

13. The removal insert of claim 12, wherein said engagement portion includes a threaded post adapted to engage a threaded bore in the device disposed within bone.

14. The removal insert of claim 12, wherein said engagement portion includes:

a ring sized to be received within an opening in an end of the device disposed within bone; and at least one engagement tab projecting outwardly from said ring.

15. The removal insert of claim 12, in which the removal tool includes a threaded post and wherein said conical portion defines a threaded bore for threaded engagement with the post of the removal tool.

* * * * *